(12) United States Patent
Endress et al.

(10) Patent No.: US 6,375,633 B1
(45) Date of Patent: Apr. 23, 2002

(54) HEEL CARE DEVICE AND METHOD

(75) Inventors: Scott A. Endress, Orchard Park; Gregory J. Pepe, Cheektowaga; Richard Buchanan, Hamburg; Keith E. Martin, Orchard Park, all of NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 09/563,608

(22) Filed: May 2, 2000

(51) Int. Cl.[7] .................................................. A61F 5/00
(52) U.S. Cl. ............................ 602/23; 602/27; 128/882
(58) Field of Search ........................... 128/846, 869, 128/882, 892, 894, DIG. 20; 602/5, 13, 23, 27

(56) References Cited

U.S. PATENT DOCUMENTS

| | | | |
|---|---|---|---|
| 3,345,654 A | 10/1967 | Noble | 5/319 |
| 4,266,298 A * | 5/1981 | Graziano | 602/13 |
| 5,020,523 A | 6/1991 | Bodine | 128/80 |
| 5,277,695 A | 1/1994 | Johnson, Jr. et al. | 602/14 |
| 5,328,445 A | 7/1994 | Spahn et al. | 602/13 |
| 5,372,576 A | 12/1994 | Hicks | 602/27 |
| 5,389,065 A | 2/1995 | Johnson, Jr. | 602/27 |
| 5,403,265 A * | 4/1995 | Berguer | 602/13 |
| 5,489,259 A | 2/1996 | Jacobs et al. | 602/13 |
| 5,603,690 A | 2/1997 | Barry | 601/148 |
| 5,634,890 A * | 6/1997 | Morris | 602/166 |
| 5,954,676 A * | 9/1999 | Kramer | 602/13 |

* cited by examiner

*Primary Examiner*—Michael A. Brown
(74) *Attorney, Agent, or Firm*—Nixon Peabody LLP (57) ABSTRACT

The present invention relates to a protective and pressure normalizing device for a body extremity, having a topside, an underside and two other sides. The device has, at a minimum, an support member and a joint aperture. In each embodiment, the support member has a lower portion, an intermediate portion, and an upper portion. The lower, intermediate, and upper portions, each contact at least a part of the body extremity, except the joint of the body extremity.

39 Claims, 7 Drawing Sheets

HEEL CARE DEVICE AND METHOD

FIELD OF THE INVENTION

The present invention generally relates to devices and methods for stabilizing and supporting the foot, in particular the heel, of a human body. The invention, more specifically, is an inflatable device that provides protection for, and relieves pressure on the foot, and particularly the heel area of the foot, when the body is in a supine or semi-Fowler's position.

BACKGROUND OF THE INVENTION

U.S. Pat. No. 5,489,259 to Jacobs et al. relates to a pressure-normalizing single-chambered static pressure device for supporting and protecting a body extremity, in particular a heel. That device has an inflatable member with an exterior and interior surfaces, a plurality of seams to connect the exterior and interior surfaces together along a line corresponding to the Achille's tendon and the ankle bones, a plurality of apertures along those seams, and a nozzle.

The nozzle is an important aspect of Jacobs et al.'s device. The nozzle allows the static pressure device to be inflated when the uninflated device is applied to the body extremity. When the device is inflated to a predetermined pressure by a third party or the patient, then the device is left alone (static) and allegedly conforms to the extremity.

A problem with the present invention is that the device may be over-inflated or even under-inflated. Such results may become deleterious to the patient. To overcome this potential problem, the present invention was conceived and reduced to practice.

SUMMARY OF THE INVENTION

The present invention relates to a protective and pressure normalizing device for a body extremity, having a topside, an underside and two other sides. The device has, at a minimum, a support member and a joint aperture. In each embodiment, the support member has a lower portion, an intermediate portion, and an upper portion. The lower, intermediate, and upper portions, each contact at least a part of the body extremity.

BRIEF DESCRIPTION OF THE DRAWINGS

For a further understanding of the invention, as well as its characterizing features, reference should now be made to the accompanying drawings wherein.

DETAILED DESCRIPTION OF THE PRESENT INVENTION

It is an object of the present invention to provide a device and method for stabilizing an ankle while relieving pressure on the heel of the foot, a knee while relieving pressure on the knee of the leg, or an elbow while relieve pressure on the elbow of the arm. The knee, ankle, and elbow are collectively referred to as a flexible joint or a bendable joint. But for purposes of making this specification read easier, we will limit our discussions to the ankle and heel.

A further object of the present invention is to provide a device and method for supporting and stabilizing the ankle and heel of the foot in order to prevent shortening of the Achilles tendon, i.e., "foot drop".

Another object of the present invention is to provide a device and method for supporting and stabilizing the ankle while relieving pressure on the heel which is adaptable to fit different sized feet and can be worn on either the left or right foot.

Other objects of the present invention include minimizing pressure contact between the heel and the surface of a hospital bed. Thereby, decreasing the risk to the patient of the formation of decubitus ulcers on the heel area as a result of such contact.

A further object of the present invention is to limit contact between the foot of a patient, especially the toe area of the foot, and objects in the patient's surroundings such as sheets, blankets etc.

Figure 1:
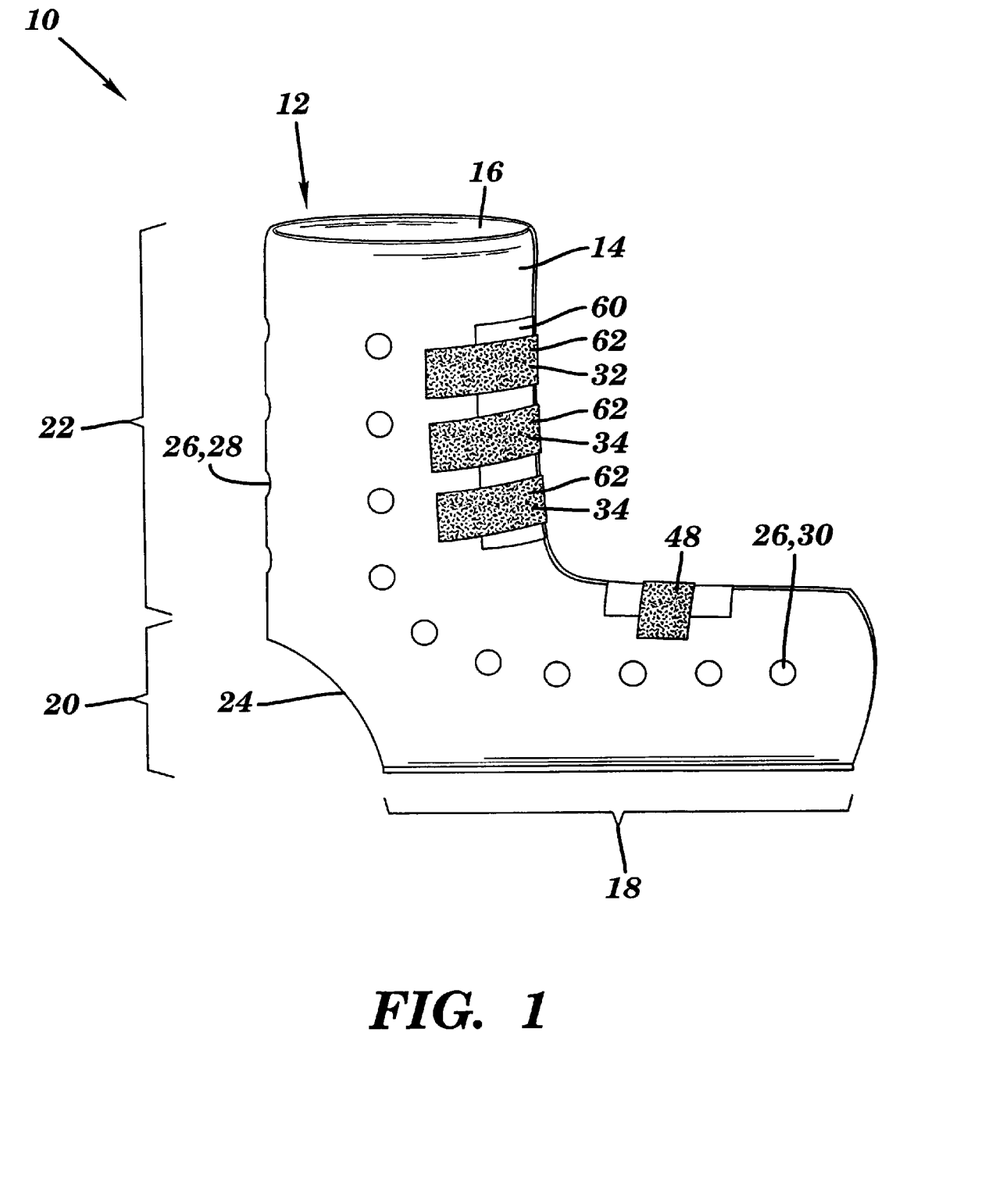
FIG. 1 is a side view of the present invention.

FIG. 1 shows a side view of a foot care device 10 according to the present invention. Foot care device 10 has at least one support surface 12, a plurality of non-support surfaces 26, at least two retaining devices 32, 34, and an aperture for a joint of a patient 24.

Turning to the support and non-support surfaces 12, 26, each of these surfaces has an interior material 16 and an exterior material 14. The interior material 16 on both surfaces 12, 26 are the same material, and the exterior material 14 on both surfaces 12, 26 are the same material. The exterior and interior materials 14, 16 can be the same or different materials.

The interior material 16 is constructed of a lightweight cotton, gauze, paper, synthetic material which may be woven or non-woven, or any other material that is breathable and suitable for use in a hospital, alternative care, or home care environment. Desirably, the material 16 is strong enough to secure a foot and leg of a patient (not shown or claimed), and capable of being comfortably placed in contact with the foot, ankle, and leg of a patient.

In contrast, the exterior material 14 can be any type of material so long as it meets some minimal characteristics. These minimal characteristics, which applies to both materials 14, 16, include not applying excessive shear force to a patient's tissue, providing adequate wicking characteristics so that moisture is drawn away from the skin of the lower leg and foot to keep the foot and leg at a normal temperature, and providing sufficient flexibility and pliability to conform readily to the shape of the patient's foot.

The device 10 is divided into at least three distinct components that correspond to a body extremity having a joint (elbow, knee or heel) of a patient (not shown or claimed). The body extremity is divided into a posterior, anterior, and the two other sides. For ease of description, we will discuss this invention, in relation to the heel of a patient. By no means, is this invention to be limited to be applied to the heel. Rather the present invention relates to elbows, and knees as well.

Returning to the components, the components are a lower portion 18, an intermediate portion 20, and an upper portion 22. The interior material 16 of the lower portion 18 contacts at least parts of the anterior and other sides of the foot. The interior material 16 of the intermediate portion 20 contacts at least a portion of the other sides of the body extremity that corresponds to the heel, which is on the posterior side of the body extremity. And the interior material 16 of the upper portion 22 contacts at least a portion of the posterior and other sides of the calf of the body extremity. Obviously, if this embodiment referred to other body extremity parts, i.e., a knee or an elbow, the respective material would contact surfaces of the body extremity other than what is disclosed above.

The joint aperture 24 exposes the heel. And if this description was related to the elbow or knee, the respective joint would be exposed in the present invention.

Figure 2:
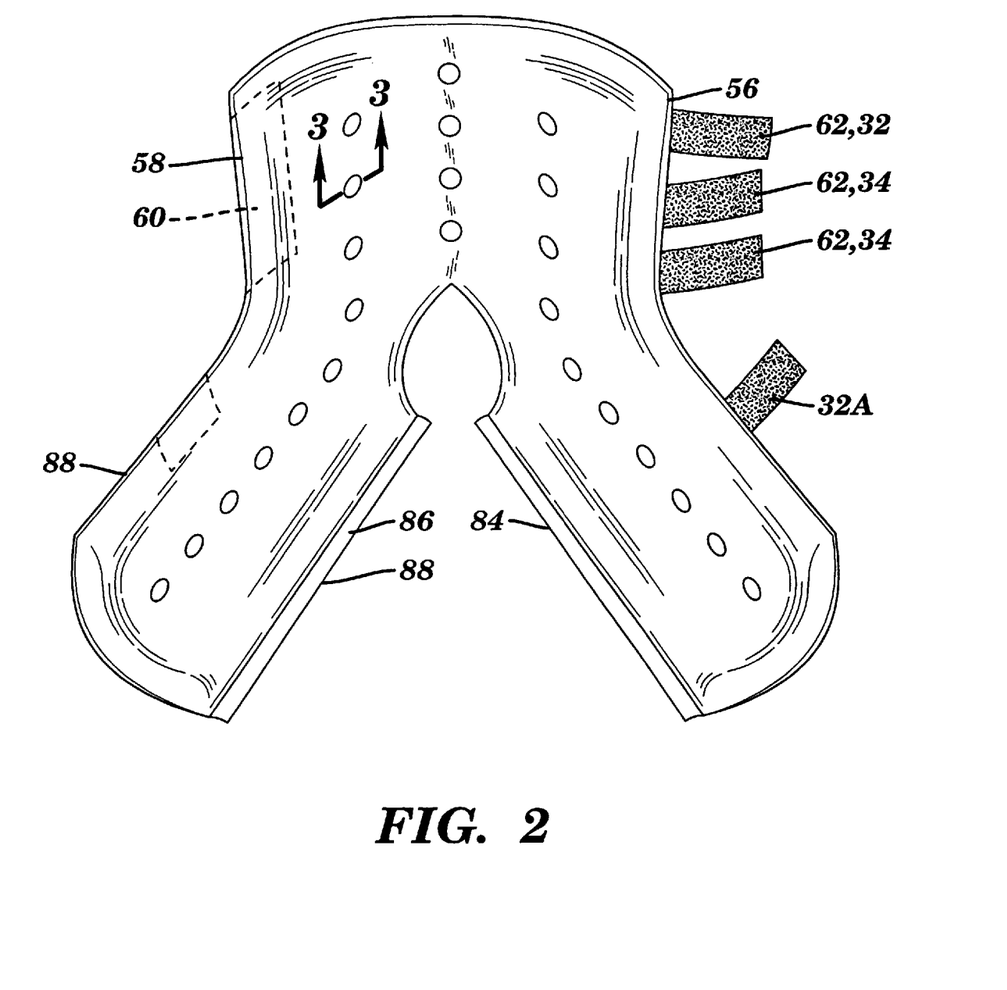
FIG. 2 is an exploded view of FIG. 1.

To relieve the pressure on the body extremity, the device 10 has a plurality of non-support members 26 interspaced throughout it. In one embodiment, shown in FIG. 1, there is a first set of non-support members 28 positioned along a line corresponding to an Achille's tendon of the calf. A second set of the non-support members 30 are positioned along a line corresponding to the an ankle bone of the body extremity. Each non-support member 28, 30 is interspaced from the others, as shown in FIG. 2, and highlighted in FIG. 3-a cross-section of FIG. 2 taken along the lines 3—3.

Figure 3:
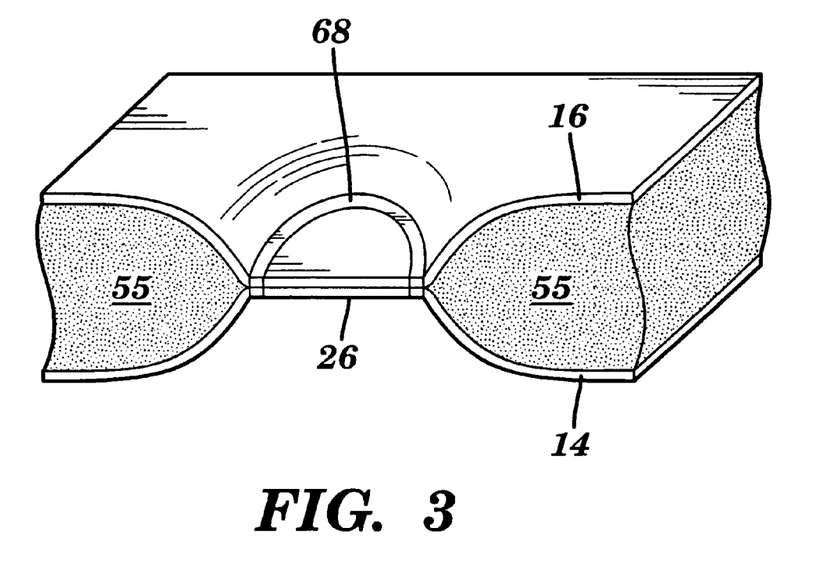
FIG. 3 is a cross-sectional view of FIG. 2 taken along the lines 3—3.
Figure 4:
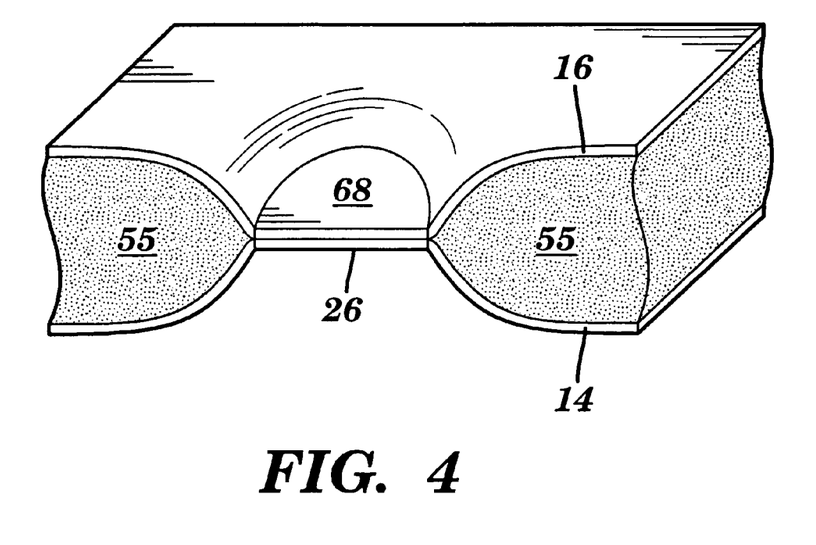
FIG. 4 is an alternative embodiment of FIG. 3.
Figure 8:
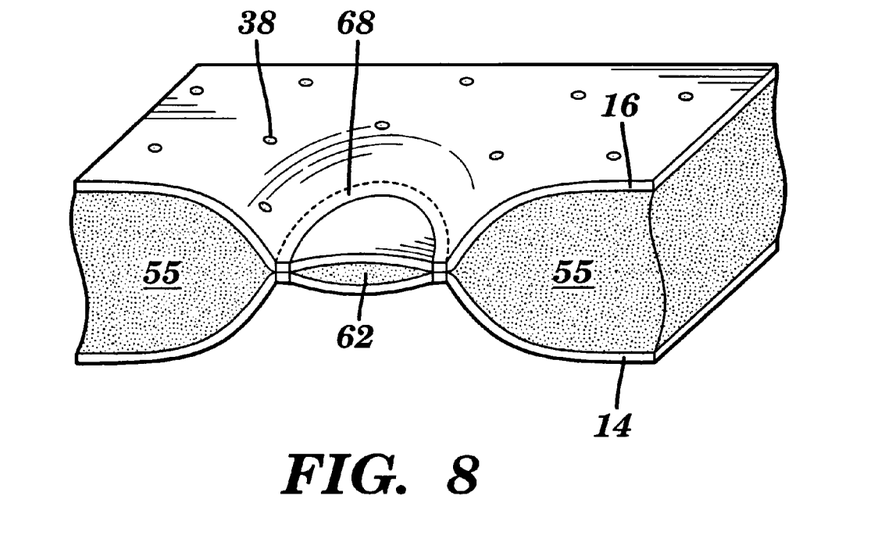
FIG. 8 is an alternative embodiment of FIG. 3.
Figure 9:
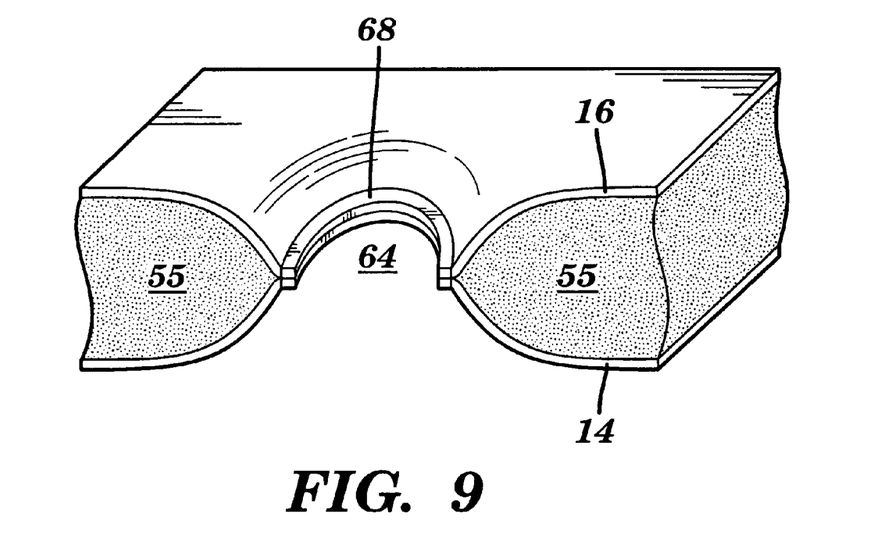
FIG. 9 is an alternative embodiment of FIG. 3.

As shown in FIG. 3, the non-support member 26 is formed by bonding predetermined portions of the interior material 16 to the exterior material 14 at predetermined point 68. In some embodiments, the predetermined point 68 is a pre-selected area of the non-support member 30 wherein the remainder of the member 30 is flat, as shown in FIG. 3, or the predetermined point 68 is the entire non-support member 30 as shown in FIG. 4 (an alternative embodiment of FIG. 3), or the predetermined point 68 is a pre-selected area of the non-support member 30 wherein the remainder of the member 30 is inflated with a gas or a predetermined piece of material 62, as shown in FIG. 8 (an alternative embodiment of FIG. 3), or the predetermined point 68 is a pre-selected area of the non-support member 30 wherein within a pre-determined portion of the remainder of the member 30 is an aperture 64, as shown in FIG. 9 (an alternative embodiment of FIG. 3). Obviously, the predetermined point 68 can be made by a heat-seal, a ultrasonic sound, or other conventional means.

As illustrated in FIGS. 3, 4, 8, and 9, the interior and exterior materials 14, 16 define a chamber 55. The chamber 55 can be filled with air, preselected gases, water, liquids, suspensions, gelastic materials, as sold by EdiZone, Inc. of Utah, or any other material that reduces the pressures on the body extremity (hereinafter collectively referred to as "Filler"). In some instances, the chamber 55 is pre-filled with Filler, preferably air, at a pre-determined pressure with no means to inflate or deflate the device 10 without destroying it. This embodiment is illustrated in FIGS. 1 and 2.

Figure 5:
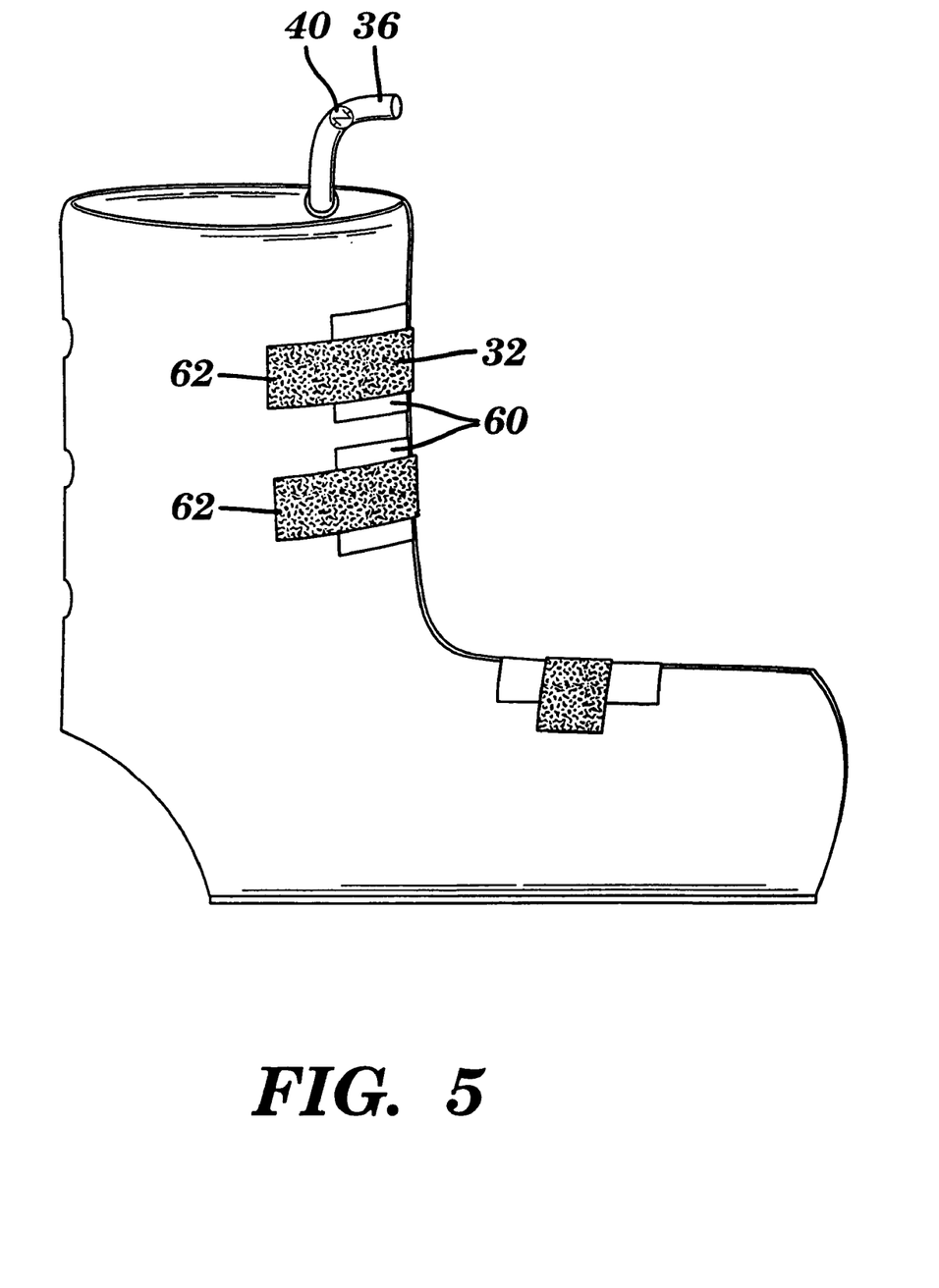
FIG. 5 is an alternative embodiment of FIG. 1.

In yet another embodiment illustrated in FIG. 5, the device 10 is pre-filled with Filler and the patient (or assistant) is able to inflate or deflate the device 10 to a desired pressure through a nozzle 36. In many instances, the nozzle 36 has a conventional check valve 40 within the nozzle 36. When this embodiment is used, the device 10 is normally pre-filled with air or air and gelastic material.

Figure 6:
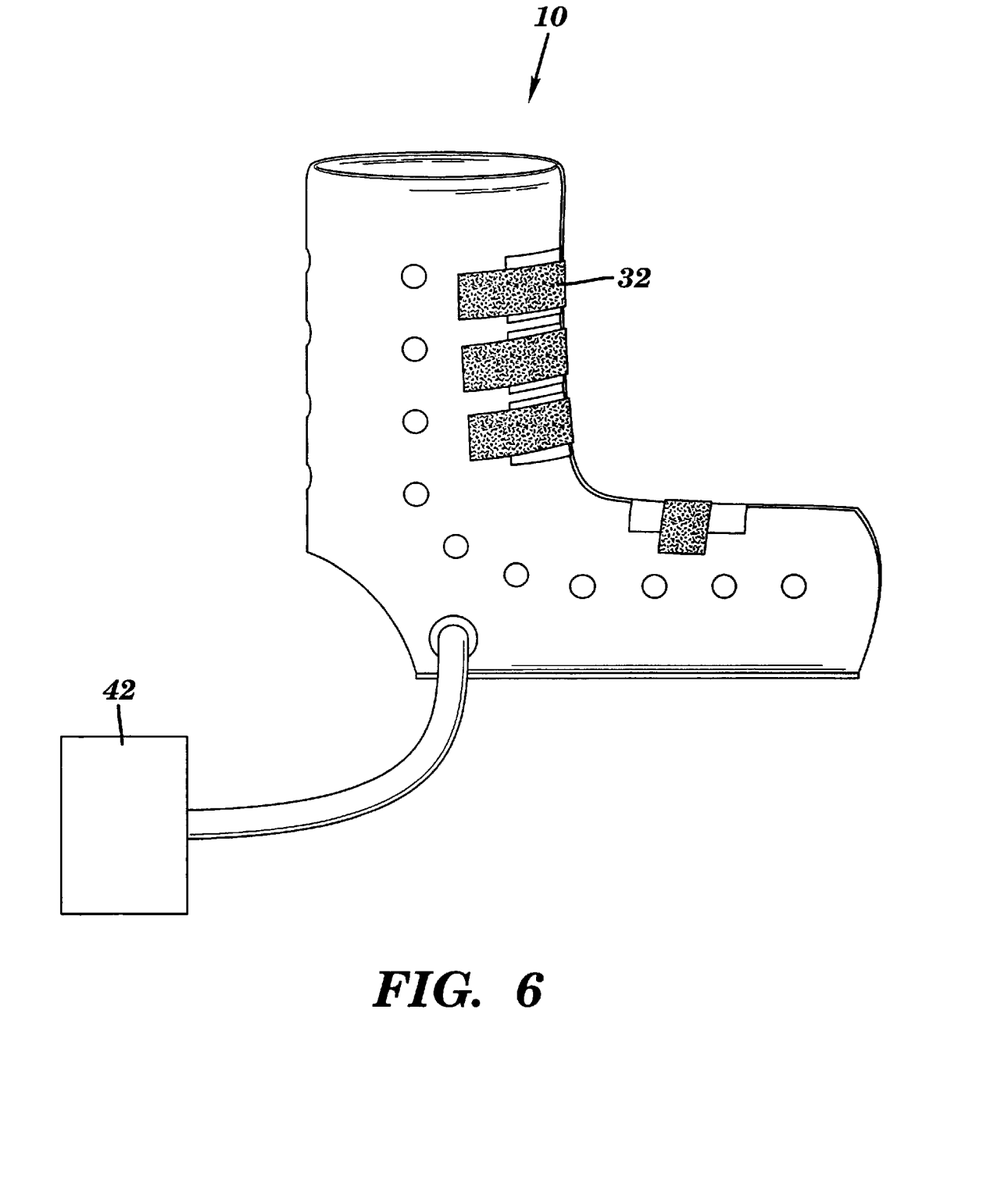
FIG. 6 is an alternative embodiment of FIG. 1.

Turning to FIG. 6, the device 10 has the same components as FIG. 5, except a pump 42 directs air into the device 10. Instead of remaining in the chamber 55, the device 10 directs the air which can be cooled air, heated air, or ambient air, to the body extremity through a plurality of apertures 38 spaced throughout the interior surface 16, as shown in figure 8. The temperature of the air is altered and pumped into device 10 for example by a THERMA-CARE air temperature unit, by Gaymar Industries, Inc. This air directed to the body extremity maintains a desired temperature, and reduces sweating to the body extremity.

Figure 7:
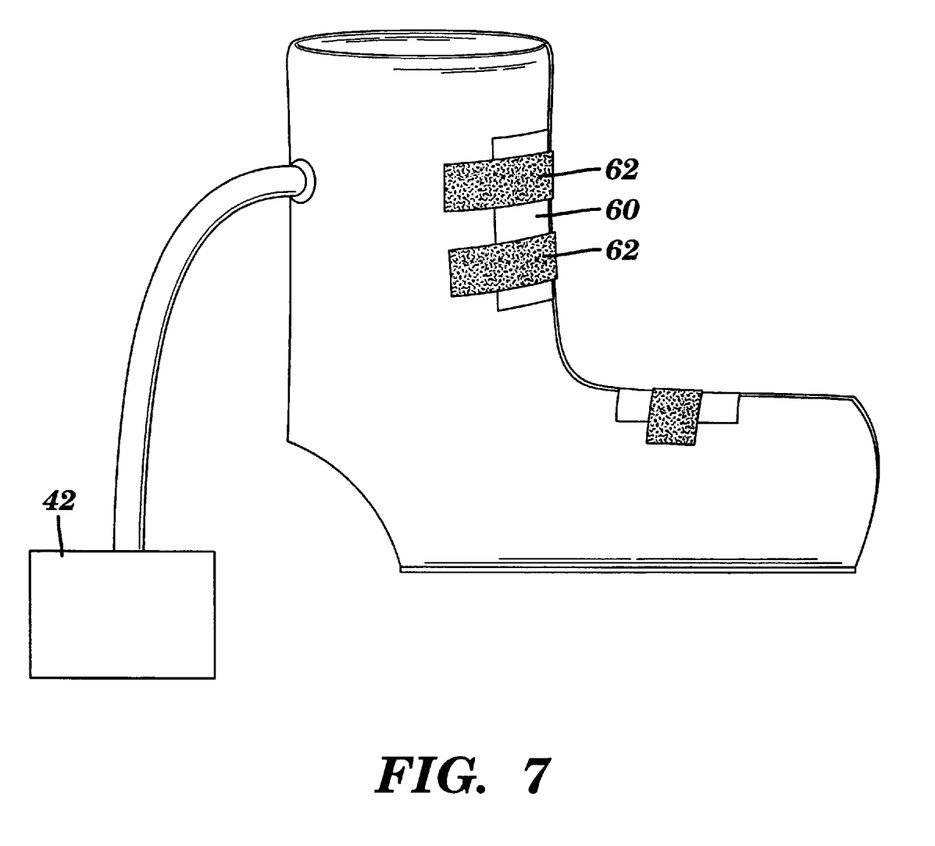
FIG. 7 is an alternative embodiment of FIG. 6.

FIG. 7 illustrates an alternative embodiment of FIG. 6 without any non-support members 26.

Reverting to FIG. 2, each embodiment of the present invention has a plurality of retaining devices 32, 34. Each retaining device 32, 34, shown in FIGS. 1, 2, and 7, is a non-support surface. In contrast, each retaining device illustrated in FIG. 6 is a support surface. In either embodiment, each retaining device 32, 34 secures the edges 56, 58 of upper section 22 to within a desired distance of each other and prevents device 10 from disengaging with the body extremity. Each retaining device 32, 34 is divided into two units, a receiver 60, and an extender 62. The extender 62 protrudes from edge 56. In contrast, receiver 60 receives the extender 62 and secures the extender 62 into a desired position. In the present embodiment, the receiver 60 is a loop device, and the extender 62 has a hook device that connects with the loop device. And the receiver 60 can be a single unit, as illustrated in FIGS. 1, 2, and 7, or separate units for each extender, as illustrated in FIG. 5, and 6.

To attain maximum engagement between the edges 56, 58, each retaining device 32, 34, in each embodiment has a particular position. The extender 62 of retaining device 32 protrudes from edge 56 at a 90° angle. Thereby, receiver 60 receives retaining device 62,32 at a 90° angle. In contrast, each subsequent retaining device 34 on the upper portion 22 has its extender angled, relative to retaining device 32 and edge 56, between greater than 45° and less than 90°. Thereby, receiver 60 receives extender 62 of retaining device 32 at a 90° angle.

Alternatively, an alternative retaining device 32a can be found, if desired, on the lower section 18 of the device 10. This alternative retaining device 32a further secures the device 10 to the body extremity.

The device 10 illustrated in FIG. 2 is in a pre-assembled position. The device 10 is put together by joining the interior material 16 to the exterior material at the edge 88. Once the edges 88 are sealed, normally by heat sealing, the two particular edges, called out as 84 and 86, are further joined together to form the device 10.

Unlike most embodiments, the present invention is pre-filled. By pre-filling the device 10, the patient is less likely to cause damage to its body extremity. Many individuals, including doctors and nurses, ignore the obvious fact that when the temperature and/or air pressure of the environment is altered the pressure within the device 10 is also altered. Therefore, by pre-filling the device 10, the doctors or nurses are unable to over inflate or under inflate the device 10.

In contrast, the embodiment illustrated in FIGS. 6 and 7 is designed to attain a pre-determined pressure greater than 0.1 psi, and preferably 0.9 to 1.0 psi—the pressure of the pre-filled device—and then allows the excess air and pressure entering the device 10 through pump 42 to escape through the apertures 38. This pressure release assists the body extremity, as set forth above, and maintains a desired pressure in the device 10. With this embodiment, the device 10 is applied to the patient, the air is pumped into the device 10 at a pre-selected pressure, and if desired and if possible, the pressure within device 10 is moderately altered. Both embodiments relieve the patient of any debucticus ulcers, provide support to the appendage.

Although a preferred embodiment of the invention has been disclosed in detail for illustrative purposes, it will be recognized that there are variations of modifications of the preferred embodiment, including the rearrangement of parts, which lie within the scope of the present invention.

We claim:

1. A protective and pressure normalizing device for a body extremity which includes a joint comprising:
   a support member having an exterior surface and an interior surface which define a chamber, wherein at least a portion of the interior surface of the support member contacts at least a portion the body extremity and wherein the support member includes a joint aperture for exposing the joint of the body extremity, and
   a plurality of apertures spaced throughout the interior surface of the support member, wherein upon communication of the chamber with a pressurized medium, at least one of the plurality of apertures directs the medium, at a pressure of greater than about 0.1 pounds per square inch within the chamber of the support member, to at least a portion of the body extremity.

2. The device according to claim 1, wherein the medium is at a pressure of from about 0.1 to about 1.0 pounds per square inch.

3. The device according to claim 1, wherein the medium is air.

4. The device according to claim 1, wherein the medium alters a temperature within the chamber to a predetermined temperature.

5. The device according to claim 1 further comprising:
   a nozzle, wherein the nozzle directs the medium into the chamber of the support member.

6. The device according to claim 5 further comprising:
   a pump to supply the medium to the nozzle.

7. The device according to claim 1, wherein the chamber comprises a single chamber.

8. The device according to claim 1 further comprising:
   a plurality of interspaced non-support members, wherein the support member surrounds each of the plurality of interspaced non-support members.

9. The device according to claim 1, wherein the support member comprises:
   a lower portion, wherein at least a portion of the interior surface of the lower portion contacts at least a portion of a lower region of the body extremity;
   an intermediate portion, wherein at least a portion of the interior surface of the intermediate portion contacts at least a portion of an intermediate region of the body extremity and wherein the intermediate portion includes the joint aperture; and
   an upper portion, wherein at least a portion of the interior surface of the upper portion contacts at least a portion of an upper region of the body extremity.

10. The device according to claim 1 further comprising:
    a plurality of securing devices, wherein the securing devices attach at least a portion of a first edge of the support member to at least a portion of a second edge of the support member under conditions effective to secure the body extremity within the support member.

11. A protective and pressure normalizing device for a body extremity which includes a joint comprising:
    a support member having an exterior surface and an interior surface which define a chamber and having a joint aperture for exposing the joint of the body extremity, wherein at least a portion of the interior surface of the support member contacts at least a portion the body extremity and wherein the interior surface comprises a wicking material.

12. The device according to claim 11, wherein the wicking material is selected from the group consisting of cotton, gauze, paper, synthetic woven material, and synthetic nonwoven material.

13. The device according to claim 11, wherein the chamber is filled with a medium to an internal pressure of greater than about 0.1 pounds per square inch.

14. The device according to claim 13, wherein the medium has an internal pressure of from about 0.1 to about 1.0 pounds per square inch.

15. The device according to claim 13, wherein the medium is air.

16. The device according to claim 13, wherein the medium alters a temperature within the chamber to a predetermined temperature.

17. The device according to claim 13 further comprising:
    a nozzle, wherein the nozzle directs the medium into the chamber of the support member.

18. The device according to claim 17, wherein the nozzle comprises a check valve.

19. The device according to claim 17, wherein the device further comprises:
    a pump to supply to medium to the nozzle.

20. The device according to claim 13 further comprising:
    a plurality of apertures spaced throughout the interior surface of the support member, wherein at least one of the plurality of apertures directs the medium from the chamber of the support member to at least a portion of the body extremity.

21. The device according to claim 11, wherein the chamber comprises a single chamber.

22. The device according to claim 11 further comprising:
    a plurality of interspaced non-support members, wherein the support member surrounds each of the plurality of interspaced non-support members.

23. The device according to claim 11, wherein the support member comprises:
    a lower portion, wherein at least a portion of the interior surface of the lower portion contacts at least a portion of a lower region of the body extremity;
    an intermediate portion, wherein at least a portion of the interior surface of the intermediate portion contacts at least a portion of an intermediate region of the body extremity and wherein the intermediate portion includes the joint aperture; and
    an upper portion, wherein at least a portion of the interior surface of the upper portion contacts at least a portion of an upper region of the body extremity.

24. The device according to claim 11 further comprising:
    a plurality of securing devices, wherein the securing devices attach at least a portion of a first edge of the support member to at least a portion of a second edge of the support member under conditions effective to secure the body extremity within the support member.

25. A method for protecting and normalizing the pressure on a body extremity which includes a joint comprising positioning the body extremity in a support member, wherein the support member comprises:
    an exterior surface and an interior surface which define a chamber, wherein the chamber includes a medium having an initial predetermined pressure and wherein the interior surface comprises a wicking material and
    a joint aperture for exposing the joint of the body extremity, wherein at least a portion of the interior surface of the support member contacts at least a portion the body extremity and wherein the joint is placed into the joint aperture.

26. The method according to claim 25, wherein the initial predetermined pressure of the medium is greater than about 0.1 pounds per square inch.

27. The method according to claim 26, wherein the initial predetermined pressure of the medium is from about 0.1 to about 1.0 pounds per square inch.

28. The method according to claim 25 further comprising:
adjusting the pressure of the medium.

29. The method according to claim 28, wherein the adjusting comprises adjusting the pressure of the medium to about 0.1 to about 1.0 pounds per square inch.

30. The method according to claim 28, wherein the adjusting comprises introducing medium into the chamber through a nozzle.

31. The method according to claim 30, wherein the nozzle comprises a check valve.

32. The method according to claim 30 further comprising:
releasing a portion of the medium to the body extremity through a plurality of apertures spaced throughout the interior surface of the support member.

33. The method according to claim 25, wherein the medium is air.

34. The method according to claim 25, wherein the medium alters a temperature within the chamber to a predetermined temperature.

35. The method according to claim 25, wherein the wicking material is selected from the group consisting of cotton, gauze, paper, synthetic woven material, and synthetic non-woven material.

36. The method according to claim 25, wherein the chamber comprises a single chamber.

37. The method according to claim 25, wherein the support member further comprises a plurality of interspaced non-support members, wherein the support member surrounds each of the plurality of interspaced non-support members.

38. The method according to claim 25, wherein the support member comprises:
a lower portion, wherein at least a portion of the interior surface of the lower portion contacts at least a portion of a lower region of the body extremity;

an intermediate portion, wherein at least a portion of the interior surface of the intermediate portion contacts at least a portion of an intermediate region of the body extremity and wherein the intermediate portion includes the joint aperture; and an upper portion, wherein at least a portion of the interior surface of the upper portion contacts at least a portion of an upper region of the body extremity.

39. The method according to claim 25, wherein the support member further comprises a plurality of securing devices, wherein the securing devices attach at least a portion of a first edge of the support member to at least a portion of a second edge of the support member under conditions effective to secure the body extremity within the support member.

* * * * *